(12) United States Patent
Leyva

(10) Patent No.: US 11,224,672 B2
(45) Date of Patent: Jan. 18, 2022

(54) SYSTEMS, METHODS, AND DEVICES FOR OZONE SANITIZATION OF CONTINUOUS POSITIVE AIRWAY PRESSURE DEVICES

(71) Applicant: SOCLEAN, INC., Peterborough, NH (US)

(72) Inventor: Timothy Leyva, Bellingham, MA (US)

(73) Assignee: SOCLEAN, INC., Peterborough, NH (US)

( * ) Notice: Subject to any disclaimer, the term of this patent is extended or adjusted under 35 U.S.C. 154(b) by 78 days.

(21) Appl. No.: 15/444,916

(22) Filed: Feb. 28, 2017

(65) Prior Publication Data

US 2017/0202990 A1    Jul. 20, 2017

Related U.S. Application Data

(60) Continuation of application No. 15/142,060, filed on Apr. 29, 2016, now Pat. No. 9,616,047, which is a
(Continued)

(51) Int. Cl.
*A61L 2/20* (2006.01)
*A61M 16/06* (2006.01)
(Continued)

(52) U.S. Cl.
CPC ............. *A61L 2/202* (2013.01); *A61L 2/183* (2013.01); *A61L 2/24* (2013.01); *A61M 16/021* (2017.08); *A61M 16/06* (2013.01); *A61M 16/0816* (2013.01); *A61M 16/0875* (2013.01); *A61M 16/1095* (2014.02); *A61M 16/16* (2013.01);
(Continued)

(58) Field of Classification Search
CPC ...................................................... A61L 2/202
See application file for complete search history.

(56) References Cited

U.S. PATENT DOCUMENTS

| 4,019,986 A | 4/1977 | Burris et al. |
| 4,035,657 A | 7/1977 | Carlson |

(Continued)

FOREIGN PATENT DOCUMENTS

| CN | 1377708 | 11/2002 |
| CN | 2710637 | 7/2005 |

(Continued)

OTHER PUBLICATIONS

U.S. Office Action dated Jun. 13, 2017, issued in U.S. Appl. No. 15/481,919, 10 pages.
(Continued)

*Primary Examiner* — Donald R Spamer
(74) *Attorney, Agent, or Firm* — Grossman, Tucker, Perrault & Pfleger, PLLC

(57) ABSTRACT

The present invention is generally related to a device and method for sanitizing a medical instrument with ozone, in particular the invention relates to a system, method and a device for sanitizing a continuous positive airway pressure (CPAP) device. The device has an ozone compartment, an ozone operating system and one or more ozone distribution lines that distribute ozone to a continuous positive airway pressure device. The device may further include a heater adapter unit to connect heating systems in CPAP devices while distributing ozone to sanitize the CPAP device in accordance with the present invention.

16 Claims, 11 Drawing Sheets

Related U.S. Application Data division of application No. 14/232,773, filed as application No. PCT/US2012/046593 on Jul. 13, 2012, now Pat. No. 9,358,316, application No. 15/444,916, which is a continuation of application No. 15/142,085, filed on Apr. 29, 2016, now Pat. No. 10,052,397, which is a continuation of application No. 14/232,773, application No. 15/444,916, which is a continuation of application No. 15/142,111, filed on Apr. 29, 2016, now Pat. No. 9,610,373, which is a continuation of application No. 14/232,773.

(60) Provisional application No. 61/508,341, filed on Jul. 15, 2011.

(51) Int. Cl.
*A61M 16/10* (2006.01)
*A61L 2/18* (2006.01)
*A61M 16/08* (2006.01)
*A61M 16/16* (2006.01)
*A61M 16/00* (2006.01)
*A61M 16/20* (2006.01)
*A61L 2/24* (2006.01)

(52) U.S. Cl.
CPC ........ *A61M 16/208* (2013.01); *A61L 2202/14* (2013.01); *A61L 2202/24* (2013.01); *A61M 16/0057* (2013.01); *A61M 16/0683* (2013.01); *A61M 2202/0216* (2013.01); *A61M 2205/27* (2013.01); *A61M 2205/502* (2013.01); *A61M 2209/10* (2013.01)

(56) References Cited

U.S. PATENT DOCUMENTS

| | | |
|---|---|---|
| 4,110,419 A | 8/1978 | Miller |
| 4,207,291 A | 6/1980 | Byrd et al. |
| 4,465,522 A | 8/1984 | Taldo et al. |
| 4,517,159 A | 5/1985 | Karlson |
| D295,074 S | 4/1988 | Jerge et al. |
| 4,743,275 A | 5/1988 | Flanagan |
| 4,787,980 A | 11/1988 | Ackermann et al. |
| 5,029,879 A | 7/1991 | Strang, Sr. et al. |
| 5,120,512 A | 6/1992 | Masuda |
| 5,207,237 A | 5/1993 | Langford |
| 5,344,622 A | 9/1994 | Faddis et al. |
| 5,508,006 A | 4/1996 | Gabele et al. |
| 5,520,893 A | 5/1996 | Kasting, Jr. et al. |
| D371,203 S | 6/1996 | Deeds |
| D390,645 S | 2/1998 | Hanrahan et al. |
| 5,761,069 A | 6/1998 | Weber et al. |
| 5,920,075 A | 7/1999 | Whitehead |
| 6,024,066 A | 2/2000 | Nakayama et al. |
| 6,134,806 A | 10/2000 | Dhaemers |
| 6,158,784 A | 12/2000 | Lavender |
| 6,276,304 B1 | 8/2001 | Tai |
| 6,280,633 B1 | 8/2001 | Conrad et al. |
| 6,365,601 B1 | 4/2002 | Fournier |
| 6,379,617 B1 | 4/2002 | Spickermann |
| 6,379,632 B1 | 4/2002 | Kinoshita et al. |
| D476,423 S | 6/2003 | Picot et al. |
| 6,576,190 B1 | 6/2003 | Park |
| 6,605,260 B1 | 8/2003 | Busted |
| D487,315 S | 3/2004 | Picot et al. |
| 6,752,151 B2 | 6/2004 | Hill |
| 7,022,225 B1 | 4/2006 | Clawson et al. |
| 7,491,321 B1 | 2/2009 | Maas |
| 7,520,910 B2 | 4/2009 | Tilley |
| 7,527,603 B2 | 5/2009 | An |
| 7,676,276 B2 | 3/2010 | Karell |
| 7,767,168 B2 | 8/2010 | Namespetra et al. |
| 7,794,522 B2 | 9/2010 | Bliss et al. |
| 7,845,350 B1 | 12/2010 | Kayyali et al. |
| 8,051,853 B2 | 11/2011 | Berthon-Jones |
| 8,146,946 B1 | 4/2012 | Emond |
| 8,176,771 B2 | 5/2012 | Onishi et al. |
| 8,431,076 B2 | 4/2013 | Fraundorfer |
| D692,155 S | 10/2013 | Matoba et al. |
| 8,770,198 B2 | 7/2014 | Yee et al. |
| 8,815,164 B1 | 8/2014 | Al Azemi |
| D719,673 S | 12/2014 | Leyva et al. |
| D719,674 S | 12/2014 | Leyva et al. |
| 8,915,380 B2 | 12/2014 | Sowerby et al. |
| 9,022,247 B2 | 5/2015 | Enigmann |
| D733,315 S | 6/2015 | Lui |
| D733,316 S | 6/2015 | Lui |
| D748,280 S | 1/2016 | Lui |
| 9,358,316 B2 | 6/2016 | Leyva |
| D761,142 S | 7/2016 | Golta et al. |
| 9,402,928 B2 | 8/2016 | Tremblay |
| D776,290 S | 1/2017 | Wan et al. |
| 9,610,373 B2 | 4/2017 | Leyva |
| 9,616,147 B2 | 4/2017 | Leyva |
| 9,669,124 B2 | 6/2017 | Leyva et al. |
| D802,788 S | 11/2017 | Cormier et al. |
| 9,895,461 B2 | 2/2018 | Leyva et al. |
| 9,907,872 B2 | 3/2018 | Schmidt et al. |
| D819,190 S | 5/2018 | Cormier et al. |
| 10,052,397 B2 | 8/2018 | Leyva |
| 10,232,072 B2 | 3/2019 | Leyva et al. |
| 10,264,913 B2 | 4/2019 | Leyva |
| 10,398,797 B2 | 9/2019 | Leyva |
| 10,427,961 B2 | 10/2019 | Leyva et al. |
| 10,434,204 B2 | 10/2019 | Leyva et al. |
| 10,434,205 B2 | 10/2019 | Leyva |
| 10,456,492 B2 | 10/2019 | Leyva |
| 10,485,888 B2 | 11/2019 | Schmidt et al. |
| 2003/0000966 A1 | 1/2003 | Shelton |
| 2003/0063997 A1 | 4/2003 | Fryer et al. |
| 2003/0065292 A1 | 4/2003 | Darouiche et al. |
| 2003/0065297 A1 | 4/2003 | Davis et al. |
| 2003/0071069 A1 | 4/2003 | Shelton |
| 2004/0251125 A1 | 12/2004 | Yu |
| 2005/0017380 A1 | 1/2005 | Namespetra et al. |
| 2005/0019237 A1 | 1/2005 | Riley |
| 2005/0186108 A1 | 8/2005 | Fields |
| 2005/0220665 A1 | 10/2005 | Ding |
| 2006/0130834 A1 | 6/2006 | Chen |
| 2006/0272682 A1 | 12/2006 | Langford |
| 2007/0031778 A1 | 2/2007 | Helfenbein et al. |
| 2007/0065335 A1 | 3/2007 | Bedard et al. |
| 2008/0050290 A1 | 2/2008 | Yui |
| 2009/0080809 A1 | 3/2009 | Pham |
| 2009/0267242 A1 | 10/2009 | Nichols et al. |
| 2010/0111792 A1 | 5/2010 | Nelson |
| 2010/0112677 A1 | 5/2010 | Onishi et al. |
| 2010/0147302 A1 | 6/2010 | Selvarajan et al. |
| 2011/0031081 A1 | 2/2011 | Iceberg |
| 2012/0164025 A1 | 6/2012 | Stockley, III et al. |
| 2012/0227745 A1 | 9/2012 | Arcilla et al. |
| 2013/0239994 A1 | 9/2013 | Przyjemski |
| 2014/0112837 A1 | 4/2014 | Huang |
| 2014/0154134 A1 | 6/2014 | Leyva |
| 2015/0004061 A1 | 1/2015 | Kain et al. |
| 2016/0235875 A1 | 8/2016 | Schmidt et al. |
| 2017/0165443 A1 | 6/2017 | Leyva |
| 2017/0202990 A1 | 7/2017 | Leyva |
| 2017/0209610 A1 | 7/2017 | Leyva et al. |
| 2017/0224857 A1 | 8/2017 | Leyva et al. |
| 2017/0225985 A1 | 8/2017 | Leyva et al. |
| 2018/0161466 A1 | 6/2018 | Schmidt et al. |
| 2018/0311391 A1 | 11/2018 | Leyva |
| 2019/0076561 A1 | 3/2019 | Leyva et al. |
| 2019/0076562 A1 | 3/2019 | Schmidt et al. |
| 2019/0083668 A1 | 3/2019 | Schmidt et al. |
| 2019/0151487 A1 | 5/2019 | Leyva |
| 2019/0167828 A1 | 6/2019 | Leyva |
| 2019/0388575 A1 | 12/2019 | Leyva et al. |
| 2020/0024167 A1 | 1/2020 | Leyva et al. |

(56) References Cited

U.S. PATENT DOCUMENTS

FOREIGN PATENT DOCUMENTS

| | | |
|---|---|---|
| CN | 2905066 Y | 5/2007 |
| CN | 201156965 | 12/2008 |
| CN | 103781498 A | 5/2014 |
| CN | 105031693 | 11/2015 |
| EP | 2731632 | 8/2017 |
| JP | 62230601 | 10/1987 |
| JP | 07027064 H | 1/1995 |
| JP | 00288091 | 10/2000 |
| JP | 2005270589 | 10/2005 |
| JP | 09131354 | 6/2009 |
| KR | 1020040098412 | 11/2004 |
| WO | 03068274 | 8/2003 |
| WO | 2008116165 | 9/2008 |
| WO | 2011058472 | 5/2011 |
| WO | 2013/012696 A1 | 1/2013 |
| WO | 2013012696 | 1/2013 |
| WO | 2015171730 | 11/2015 |
| WO | 2017189915 | 11/2017 |
| WO | 2017189916 | 11/2017 |
| WO | 2018200525 | 11/2018 |

OTHER PUBLICATIONS

International Search Report and Written Opinion dated Aug. 2, 2017, issued in PCT Patent Application No. PCT/US17/29949, 11 pages.
U.S. Office Action dated Aug. 3, 2017, issued in U.S. Appl. No. 15/141,152, 14 pages.
International Search Report and Written Opinion dated Aug. 16, 2017, issued in PCT Patent Application No. PCT/US17/29950, 11 pages.
Office Action dated Sep. 21, 2017, issued in U.S. Appl. No. 15/142,085, 9 pages.
Notice of Allowance dated Oct. 13, 2017, issued in U.S. Appl. No. 15/481,919, 7 pages.
U.S. Final Office Action dated Feb. 5, 2018, issued in U.S. Appl. No. 15/141,152, 16 pages.
U.S. Office Action dated Apr. 3, 2018, issued in U.S. Appl. No. 15/873,506, 7 pages.
U.S. Notice of Allowance dated Apr. 27, 2018, issued in U.S. Appl. No. 15/142,085, 8 pages.
International Search Report and Written Opinion dated Jul. 13, 2018, issued in PCT International Patent Application No. PCT/US18/29140, 12 pages.
Office Action dated Aug. 9, 2018, issued in Japanese Patent Application No. 2014-520352, 5 pages. English language translation provided.
Office Action dated Sep. 5, 2018, issued in Chinese Patent Application No. 2016105175158, 10 pages. English language translation provided.
Office Action dated Sep. 17, 2018, issued in U.S. Appl. No. 15/441,929, 10 pages.
Examination Report dated Sep. 26, 2018, issued in Australian Patent Application No. 2017228723, 6 pages.
Office Action dated Oct. 30, 2018, issued in U.S. Appl. No. 15/499,456, 13 pages.
Notice of Allowance dated Oct. 31, 2018, issued in U.S. Appl. No. 15/873,506, 8 pages.
Office Action amendment dated Oct. 31, 2018, issued in U.S. Appl. No. 15/499,456, 13 pages.
Office Action dated Nov. 6, 2018, issued in U.S. Appl. No. 15/499,378, 18 pages.
Preliminary Report on Patentability mailed Nov. 8, 2018, issued in PCT International Patent Application No. PCT/US2017/029949, 9 pages.
Preliminary Report on Patentability mailed Nov. 8, 2018, issued in PCT International Patent Application No. PCT/US2017/029950, 9 pages.
Office Action dated Jan. 16, 2019, issued in Korean Patent Application No. 10-2018-7009274, 5 pages. English language translation provided.
Notice of Allowance dated Jan. 18, 2019, issued in U.S. Appl. No. 15/441,929, 7 pages.
Office Action dated Jan. 22, 2019, issued in U.S. Appl. No. 16/190,996, 10 pages.
CPAP Guardian TB-316, America Tyson Industrial Group (Asia Pacific) Limited, http://www.ecvv.com/products/2314441.html, Nov. 91, 2009, downloaded from Internet Jul. 8, 2016, 3 pages.
International Search Report and Written Opinion dated Sep. 17, 2012, issued in PCT Application No. PCT/US12/46593, 6 pages.
International Search Report and Written Opinion dated Jul. 24, 2015, issued in PCT Application No. PCT/US15/29418, 9 pages.
U.S. Office Action dated Jun. 30, 2016, issued in U.S. Appl. No. 15/141,216, 13 pages.
U.S. Office Action dated Jul. 13, 2016, issued in U.S. Appl. No. 15/142,060, 18 pages.
U.S. Office Action dated Jul. 14, 2016, issued in U.S. Appl. No. 15/142,111, 10 pages.
U.S. Office Action dated Jul. 28, 2016, issued in U.S. Appl. No. 15/142,085, 15 pages.
U.S. Office Action dated Oct. 6, 2016, issued in U.S. Appl. No. 15/141,152, 11 pages.
U.S. Office Action dated Nov. 23, 2016, issued in U.S. Appl. No. 15/141,216, 9 pages.
U.S. Office Action dated Nov. 23, 2016, issued in U.S. Appl. No. 15/142,085, 8 pages.
U.S. Office Action dated Feb. 23, 2017, issued in U.S. Appl. No. 29/562,755, 8 pages.
U.S. Office Action dated Feb. 27, 2017, issued in U.S. Appl. No. 29/562,756, 7 pages.
U.S. Office Action dated Mar. 17, 2017, issued in U.S. Appl. No. 15/141,152, 14 pages.
Final Office Action dated Feb. 4, 2019, issued in U.S. Appl. No. 15/141,152, 14 pages.
Examination Report dated Feb. 15, 2019, issued in Australian Patent Application No. 2018200514, 5 pages.
Notice of Allowance dated Apr. 30, 2019, issued in U.S. Appl. No. 15/441,929, 5 pages.
Office Action dated Mar. 4, 2019, issued in U.S. Appl. No. 16/257,898, 13 pages.
Office Action dated Mar. 14, 2019, issued in U.S. Appl. No. 16/270,141, 12 pages.
Notice of Allowance dated Mar. 19, 2019, issued in U.S. Appl. No. 15/499,456, 12 pages.
U.S. Appl. No. 16/257,898, filed Jan. 25, 2019.
Office Action dated Apr. 2, 2019, issued in Japanese Patent Application No. 2017-0149891, 7 pages.
Examination Report dated May 15, 2019, issued in Australian Patent Application No. 2017228723, 5 pages.
Notice of Allowance dated May 17, 2019, issued in U.S. Appl. No. 16/270,141, 7 pages.
Notice of Allowability dated May 22, 2019, issued in U.S. Appl. No. 15/499,456, 5 pages.
Notice of Allowance dated May 28, 2019, issued in U.S. Appl. No. 15/499,378, 7 pages.
Notice of Allowance dated Jun. 20, 2019, issued in U.S. Appl. No. 16/257,898, 8 pages.
U.S. Office Action dated Jul. 26, 2019, issued in U.S. Appl. No. 16/190,996, 12 pages.
Office Action dated Feb. 3, 2020, issued in U.S. Appl. No. 16/190,996, 9 pages.
Office Action dated Feb. 18, 2020, issued in Canadian Patent Application No. 3,005,981, 3 pages.
Office Action dated Mar. 19, 2020, issued in Korean Patent Application No. 10-2020-7003298, 4 pages.
Office Action dated Mar. 23, 2020, issued in Chinese Patent Application No. 2017101790491, 8 pages.
Office Action dated Apr. 7, 2020, issued in U.S. Appl. No. 16/780,492, 13 pages.
Office Action dated Apr. 13, 2020, issued in U.S. Appl. No. 16/782,892, 15 pages.

(56) References Cited

OTHER PUBLICATIONS

Notice of Allowance dated Apr. 28, 2020, issued in U.S. Appl. No. 16/780,492, 7 pages.
Office Action dated Apr. 23, 2020, issued in U.S. Appl. No. 16/780,355, 14 pages.
VPAP IV and VPAP IV ST Product Training ("ResMed Presentation"). Cited by opposing counsel in connection with SoClean Inc. v. Sunset Healthcare Solutions, Inc., Civil action No. 1:20-cv-10351-IT (U.S. Dist. Ct. Massachusetts). Publication Date is unknown to Applicant, but was asserted by opposing counsel in the noted litigation to be in 2008.
Examination Report dated Jun. 7, 2019, issued in Canadian Patent Application No. 3,005,981, 3 pages.
Preliminary Report on Patentability mailed Nov. 7, 2019, issued in PCT Patent Application No. PCT/US2018/029140, 11 pages.
Notice of Allowance dated Nov. 15, 2019, issued in Australian Patent Application No. 2018200514, 4 pages.
Extended Search Report dated Nov. 29, 2019, issued in European Patent Application No. 17790471.1, 9 pages.
Examination Report dated Jan. 13, 2020, issued in Chilean Patent Application No. 201803063, 17 pages. English language machine translation included.
Office Action dated Jul. 29, 2019, issued in Chinese Patent Application No. 2017101786091, 10 pages.
Office Action dated Jul. 29, 2019, issued in Chinese Patent Application No. 2017101790472, 8 pages.
Office Action dated Aug. 6, 2019, issued in Chinese Patent Application No. 2017101795495, 9 pages.
Notice of Allowance dated Aug. 8, 2019, issued in U.S. Appl. No. 15/141,152, 8 pages.
Examination Report dated Aug. 13, 2019, issued in Australian Patent Application No. 2018200514, 6 pages.
Notice of Acceptance dated Aug. 14, 2019, issued in Australian Patent Application No. 2017228723, 4 pages.
Notice of Allowance dated Oct. 8, 2019, issued in Japanese Application No. 2017-149891, 4 pages.
China Office Action from related matter CN201780025983.6 dated May 9, 2020, with English translation.
China Office Action from related matter CN201710179459.5 dated May 29, 2020, with English translation.
International Search Report and Written Opinion from related matter PCT/US20/23631 dated Jun. 3, 2020.
China Office Action from related application CN 201710186091 dated Jul. 1, 2020, with English translation.
China Office Action from related application CN 20171017904.2 dated Jul. 1, 2020, with English translation.
China Office Action from related application CN 201710178638.8 dated Jul. 3, 2020, with English translation.
U.S. Office Action from related matter U.S. Appl. No. 16/191,059 dated Jun. 11, 2020.
U.S. Final Office Action from related matter U.S. Appl. No. 16/294,097 dated Jun. 11, 2020.
U.S. Office Action from related matter U.S. Appl. No. 15/880,962 dated Jun. 11, 2020.
Goodknight 420G Patient Manual, 2005 Nellcor Puritan Bennett Inc.
SoClean 2 PAP Disinfecting Device User Guide Copyright 2011-2014, Inceptus, Inc.
CPAP Guardian. Retrieved from http://www.ecvv.com/product/2314441 html, Aug. 19, 2021.
Chaunet et al., "The sterilization technology for the 21st century," TS03, Inc. 2007.
Dhkawa et al. "High grade disinfection using high-density ozone," J Adv Oxid Tech, 7, 154-160, (2004).
"Keep your CPAP machine clean and safe," Oct. 18, 2010—Available at https://www.cpap.co.uk/2010/10/keep-your-cpap-machine-clean-and-safe.
GoodKnight H20 Heated Humidifier User's Manual, 2006 Nellcor Puritan Bennett.
Hoffrichter Trend II User's Manual (date unknown).
Hudson RCI Product Catalog (2004-2005).
KnightStar(R) 330 User's Manual, 2006, Nellcor Puritan Bennett.
DeVilbiss® DV54 AutoAdjust CPAP Series (DeVilbiss® SleepCube Positive Airway Pressure Device) User Manual 2009). Available at https://www.manualslib.com/manual/1577762/Devilbiss-Intellipap-Dv54.html.
Sunset Healthcare Solutions, Inc's Preliminary Patent Disclosures Pursuant to Local Rule 16.6(d)(4) in SoClean, Inc. v Sunset Healthcare Solutions, Inc, in Civil Action No. 1:20-cv-10351-IT.
Sunset Healthcare Solutions, Inc's Second Amended Counterclaims in SoClean, Inc.v. Sunset Healthcare Solutions, nc,in Civil Action No. 1:20-cv-10351-IT and Consolidated Case No. 1:21-cv-1013IT.
Memorandum in Support of SoClean's Motion to Dismiss Counts Eight and Nine of Sunset's Second Amended Counterclaims, SoClean, Inc.v. Sunset Healthcare Solutions, Inc,in Civil Action No. 1:20-cv-10351-IT and Consolidated Case No. 1:21-cv-1013IT.
Defendant Sunset's Memorandum in Opposition to SoClean's Motion to Dismiss Counts Eight and Nine of Sunset's Second Amended Counterclaims. C.A No. 1:20-cv-10351-IT. Filed Aug. 6, 2021.
ResMed VPAP III ST-A with QuickNav Clinical Guide, copyright 2008 ("ResMed Guide"). Cited by opposing counsel in connection with SoClean Inc.v. Sunset Healthcare Solutions, Inc., Civil action No. 1:20-cv-10351-IT (U.S. Dist. Ct. Massachusetts).
VPAP IV and VPAP IV ST Product Training ("ResMed Presentation"). Cited by opposing counsel in connection with SoClean Inc.v. Sunset Healthcare Solutions, Inc., Civil action No. 1:20-cv-10351-T (U.S. Dist. Ct. Massachusetts). Publication Date is unknown to Applicant, but was asserted by opposing counsel in the noted litigation to be in 2008.
Lenntech "Ozone Generation", Wayback Machine Capture, Mar. 28, 2010, (Year 2010), 3 pages.
Ozone Msds (Material Safety Data Sheets), Ozone Solutions, Jun. 1, 2000, http://www.ozoneapplications.com/info/ozone_msds.htm, 5 pages.
Office Action dated Apr. 28, 2021 in JP 2019-201674, 3 pages.
Office Action mailed Jul. 3, 2020, issued in Chinese Patent Application No. 2017101786388, 8 pages. English anguage translation provided.
First Examination Report issued in Indian Patent Application No. 60/MUMNP/2014, dated Jul. 10, 2019, 6 pages.
Office Action dated Nov. 18, 2020 in CN 201780025983.6.
Office Action dated May 18, 2021 in CN 201780025983.6.
Office Action dated Nov. 1, 2020 in KR 10-2020-7026960,2 pages.
Office Action dated Jul. 26, 2021, issued in Chinese Patent Application No. 2017101790472,4 pages. English anguage translation provided.
Office Action dated May 29, 2020, issued in Chinese Patent Application No. 2017101795495,4 pages. English anguage translation provided.
Office Action dated Jul. 1, 2020, issued in Chinese Patent Application No. 2017101790472,4 pages. English anguage translation provided.
Office Action dated Jul. 3, 2020, issued in Chinese Patent Application No. 2017101786388, 8 pages. English anguage translation provided.
Restriction Requirement issued in related U.S. patent application No. 17/025,6334, mailed Aug. 2, 2021 (6 pages).
Office Action dated May 11, 2021 in BR112018-071444-5.

SYSTEMS, METHODS, AND DEVICES FOR OZONE SANITIZATION OF CONTINUOUS POSITIVE AIRWAY PRESSURE DEVICES

CROSS-REFERENCE TO RELATED APPLICATIONS

This application is a continuation of U.S. patent application Ser. No. 15/142,060 (now U.S. Pat. No. 9,616,047), U.S. patent application Ser. No. 15/142,085 (now U.S. Pat. No. 10,052,397), and U.S. patent application Ser. No. 15/142,111 (now U.S. Pat. No. 9,610,373). U.S. patent application Ser. Nos. 15/142,085 and 15/142,111 are each a continuation of U.S. patent application Ser. No. 14/232,773 (now U.S. Pat. No. 9,358,316), and U.S. patent application Ser. No. 15/142,060 is a divisional of U.S. patent application Ser. No. 14/232,773 (now U.S. Pat. No. 9,358,316). U.S. patent application Ser. No. 14/232,773 is a National Phase Application under 35 U.S.C. § 371 of International Application No. PCT/US12/46593, filed Jul. 13, 2012, which claims priority to U.S. Provisional Application Ser. No. 61/508,341, filed Jul. 15, 2011. The disclosure of all such prior applications is incorporated herein by reference.

FIELD OF THE INVENTION

The present invention is generally related to a device and method for disinfecting a medical instrument with ozone, in particular the invention relates to a device and method for disinfecting a continuous positive airway pressure (CPAP) device.

BACKGROUND OF THE INVENTION

Sleep apnea is a common sleep disorder characterized by abnormal breathing during sleep. Pauses in breathing for people with sleep apnea can last from a few seconds to minutes during sleep, often resulting in significant levels of sleep disturbance, which may result in daytime fatigue, impaired reaction time, vision problems, and impaired daytime cognition.

Sleep apnea is often treated with a continuous positive airway pressure (CPAP) device. CPAP devices prevent reduction of oxygen levels in the blood and sleep loss by delivering a stream of pressured air through a hose to a nasal pillow or full facemask surrounding a patient's nose. The CPAP devices work by blowing air at a prescribed pressure for each patient, and keeping the air passage open to maintain unobstructed breathing throughout a sleep period.

While CPAP treatment can be a highly effective treatment for sleep apnea, a major downside with CPAP treatment is non-compliance by users. Users are often reluctant to continuously use CPAP devices because the nose and face masks may be uncomfortable. In addition, maintenance of many CPAP devices has proved to be tiring and difficult for users, as water vapor running through the hoses and masks of a device may cause bacterial build-up and require continuous cleaning and prevention as necessary steps to safely use a device, which may result in further non-compliance by users. Most manufacturers of CPAP devices recommend that users perform daily and weekly maintenance on their machines to prevent bacteria and mold buildup. In this instance, each part of the CPAP device needs to be cleaned individually, including the mask, the hoses and the humidification portion, which is difficult and time consuming for users on a daily or weekly basis. Other CPAP device cleaning methods include soaking the component parts of a CPAP device in a mixture of vinegar and water to disinfect the component parts. Because of the inherent nature for CPAP devices to collect bacteria and mold, a number of other products are available to consumers to make CPAP machines safer, including but not limited to:

Citrus II Cleaning Spray for masks and tubing, available at www.cpapxchange.com

Contour CPAP cleaning wipes

CPAP tube cleaning brushes, available at www.cpapxchange.com

CPAP Guardian, available at www.cpapguardian.com

Further, several patents and patent applications have been filed on CPAP devices, improvements and the like. The patents in the field of CPAP devices include U.S. Pat. Nos., 8,146,946, 8,051,853, 7,794,522, 7,845,350, 7,676,276, 6,276,304, 7,527,603, 7,767,168, 6,752,151, 6,280,633, 7,022,225, 4,787,980 and US application numbers: 20100111792, 20060130834, 20040251125, 20050186108.

While some of the existing products, patents and applications described above refer to CPAP systems, methods and devices, there is no system, method or device shown that describes an automated disinfecting system or method for a CPAP device, for ease of use of users and to improve user compliance. In addition, the use of ozone to sanitize, disinfect and clean CPAP devices is a long felt need in the art as a safe and easy disinfectant system for improved compliance of a user, as described in accordance with the present invention.

Other systems, methods, device features, and advantages of the present invention will be or become apparent to one with skill in the art upon examination of the following drawings and detailed description. It is intended that all such additional systems, methods, device features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

Figure 1:
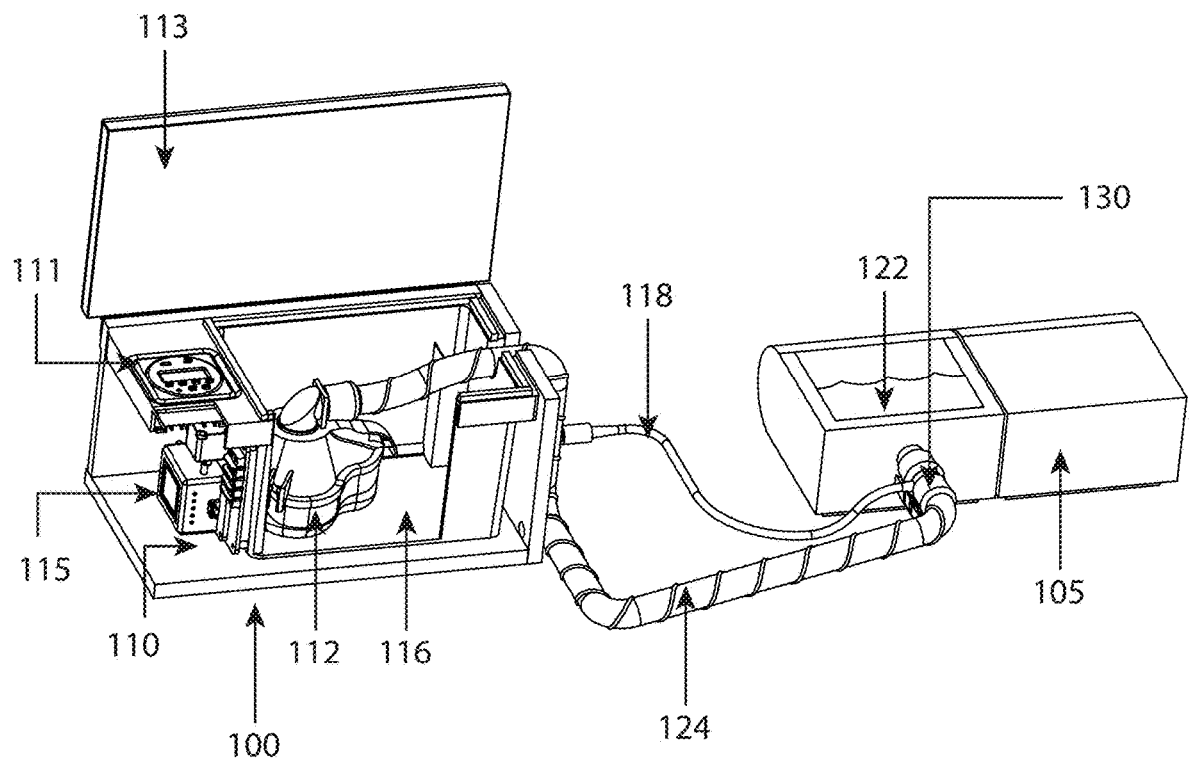
FIG. 1 is a perspective view of an ozone device connected to a CPAP device, in accordance with one embodiment of the invention.

FIG. 1 shows a perspective view of an ozone device 100 connected to a CPAP device 105. In this embodiment an ozone compartment 110 for housing an ozone operating system 115 is shown in the ozone device 100. In accordance with this embodiment, the ozone operating system 115 produces and transfers ozone to the CPAP device 105 to disinfect the CPAP device 105 before or after use by a user.

In accordance with this embodiment, the ozone operating system 115 pulls in ambient air into an air pump to create ozone. The air pump may transfer the ambient air to a corona discharge ozone generator, which may create about 400 mg/hr of ozone gas, which may be used to disinfect a CPAP device 105. In accordance with this embodiment, the ozone may be pumped directly into the CPAP device 105 and/or a water reservoir tank 122 from the ozone compartment 110 through an ozone distribution line 118 that connects to the CPAP connector unit 130, for providing ozone to disinfect the CPAP device 105. In accordance with the device shown in FIG. 1 the ozone may enter the ozone distribution line 118 when powered by a small air pump, such as an aquarium pump, and then migrate through the distribution line 118, through a CPAP connector unit 130, and into the water reservoir 122. The ozone distribution line 118 traverses into the hose 124 and the CPAP connector unit 130 and ends with a free end immersed in the CPAP water reservoir 122. The ozone may then be released into water in the water reservoir 122, acting to disinfect and sanitize the water reservoir 122, and may then release as free ozone from the water in the water reservoir 122. The free ozone may then traverse into the hose 124, which then carries the ozone into a mask compartment 116 to sanitize a mask 112. Within about 20-30 minutes from the start of the ozone sanitizing process described, the ozone will naturally breakdown into oxygen $O^2$, resulting in a CPAP device 100 with an automated disinfecting process with ozone passing through and disinfecting the CPAP water reservoir 122, the water in the reservoir, the hose 124, the mask compartment 116 and the mask 112. As an additional safety precaution to make sure all ozone is released from the CPAP device 105 before a user utilizes the CPAP device 105, an oxidizing catalyst, such as an MgO filter, may be on the ozone device 100, such as on the back side of the mask compartment 116 to collect, breakdown and release remaining ozone as oxygen $O^2$.

The ozone compartment 110, in accordance with the present embodiment of the present invention may be any available ozonator or a like device for creating ozone gas. Ozonators create ozone from oxygen molecules, often by applying ultraviolet light to the oxygen. Ozone gas is made of oxygen molecules that have been ionized by radiation to form groups of three oxygen atoms, $O^3$. The ozone gas is powerful and effective for removal of odors, impurities and dangerous pathogens, working by exchanging electron charge with particles that ozone comes into contact with to form oxygen, $O^2$, from the unstable ozone $O^3$, a process particularly useful for purifying air and water and for killing bacteria and microorganisms. Typically, ozone, $O^3$, will convert back to oxygen, $O^2$, within two hours of the start of a cycle.

In accordance with the embodiment shown in FIG. 1, a small air pump is provided in the ozone compartment 110 to push ozone into the water reservoir 122. An exhaust port is further provided in the mask compartment 116 and has two main functions; the first is to draw the free ozone up into the hose 124 from the water reservoir 122 and into the mask 112 from the water reservoir 122. The free ozone will work to disinfect the water reservoir 122, the hose 124, and the mask 112. After exiting the mask 112 the free ozone then will be drawn out of the mask compartment 116 through the exhaust port into the free atmosphere as oxygen $O^2$. Further shown in this embodiment is a user interface 111 for a user to set a sanitizing schedule on the ozone device 100 and a top cover 113 to close the ozone device 100.

Figure 2:
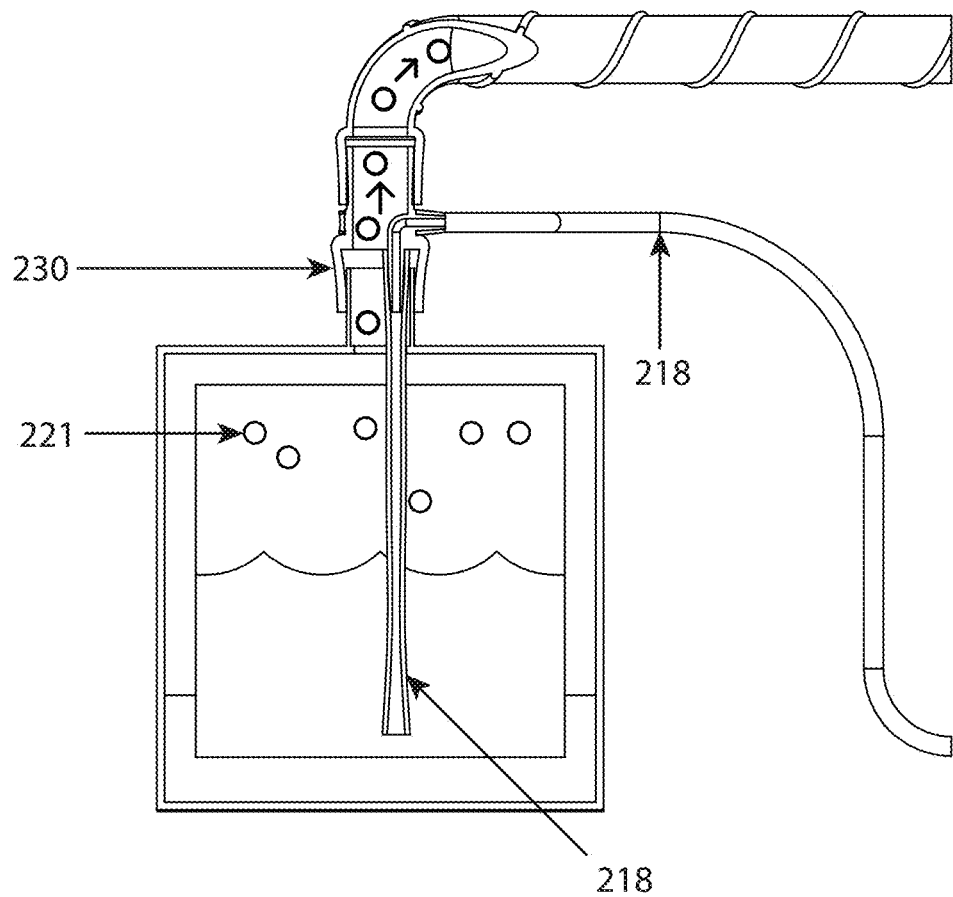
FIG. 2 is a side-view of a CPAP connector unit and a hose connecting to a water reservoir, in accordance with one embodiment of the invention.

FIG. 2 is a side view of a CPAP connector unit 230 attaching the ozone distribution line 218 from an ozone device to the water reservoir 222 of a CPAP device in accordance with another embodiment of the present invention. In accordance with this embodiment the ozone distribution line 218 is shown connected through the CPAP connector unit 230, at a ninety degree angle, and into the water reservoir 222. The ozone may be distributed from the ozone distribution line 218 into the water 219. The ozone 221 may effectively sanitize the water and kill bacteria and microorganisms in the water 219 by oxidizing organics in the water 219. Free ozone 221 that is left after removing organics from the water 219 in the water reservoir 222 may then release from the water and pass into the hose 224 to sanitize the hose and then enter a mask compartment for sanitizing a mask. By sanitizing the ozone water reservoir 222, the water 219, the hose 224 and the mask after each use, a user may effectively clean and sanitize their CPAP machines on a daily basis and use the machine with a decreased risk of discomfort, infection or bacteria growth in their CPAP device. While the CPAP device may still need to be cleaned in accordance with a manufacturer's requirements, the present invention will assist a user to maintain a safe to use device on a regular basis and improve compliance and use of the CPAP device to treat sleep apnea. The inventors expect that the current invention will assist people with sleep apnea to easily disinfect their CPAP device and use their machines safely in accordance with personal preferences and routine schedules.

Figure 3:
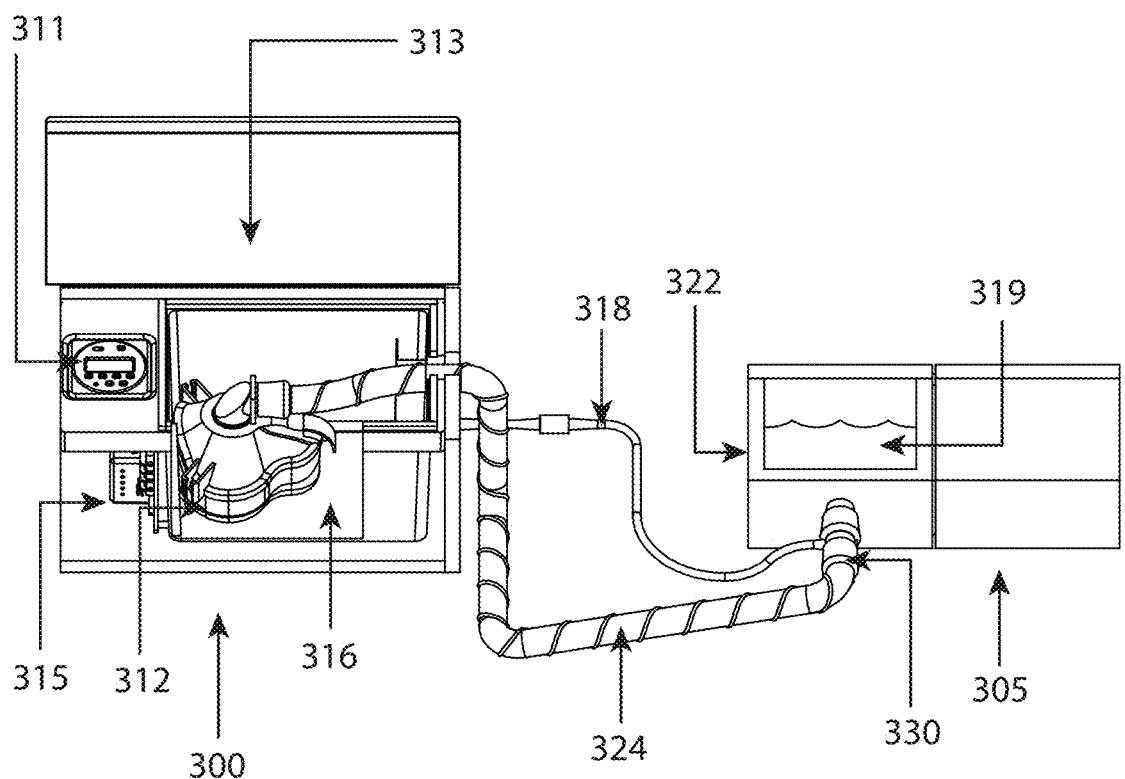
FIG. 3 is a perspective view of an ozone device connected to a CPAP device, in accordance with one embodiment of the invention.

FIG. 3 shows a front view of an ozone device 300 and a CPAP device 305 in accordance with another embodiment of the present invention. In accordance with this embodiment, an ozone operating system 315 may make ozone, which may enter the water 319 in the water reservoir 322 through the distribution line 318 and the CPAP connector unit 330. In accordance with this embodiment ozone enters the hose 324 as free ozone from the water reservoir 322, and the hose 324 carries the ozone gas to sanitize the mask 312 in the mask compartment 316. In accordance with this embodiment the ozone disinfects and sanitizes the entire CPAP device 305 for a user prior to use, including the water reservoir 322, the water 319, the hose 324, the mask 312 and the mask compartment 316. In accordance with this embodiment, the ozone may convert back to a stable form of oxygen after entering the mask compartment 316, making a user's CPAP device 305 easily disinfected and ready to use. In accordance with this embodiment an MgO exhaust port may be provided in the mask compartment 316 to collect, breakdown and release remaining ozone to the atmosphere, as an additional safety measure to make sure all ozone and free ozone is removed from the ozone device 300 prior to use. Further shown in this embodiment is a user interface 311 for a user to set a sanitizing schedule on the ozone device 300 and a top cover 313 to close the ozone device 300.

Figure 4:
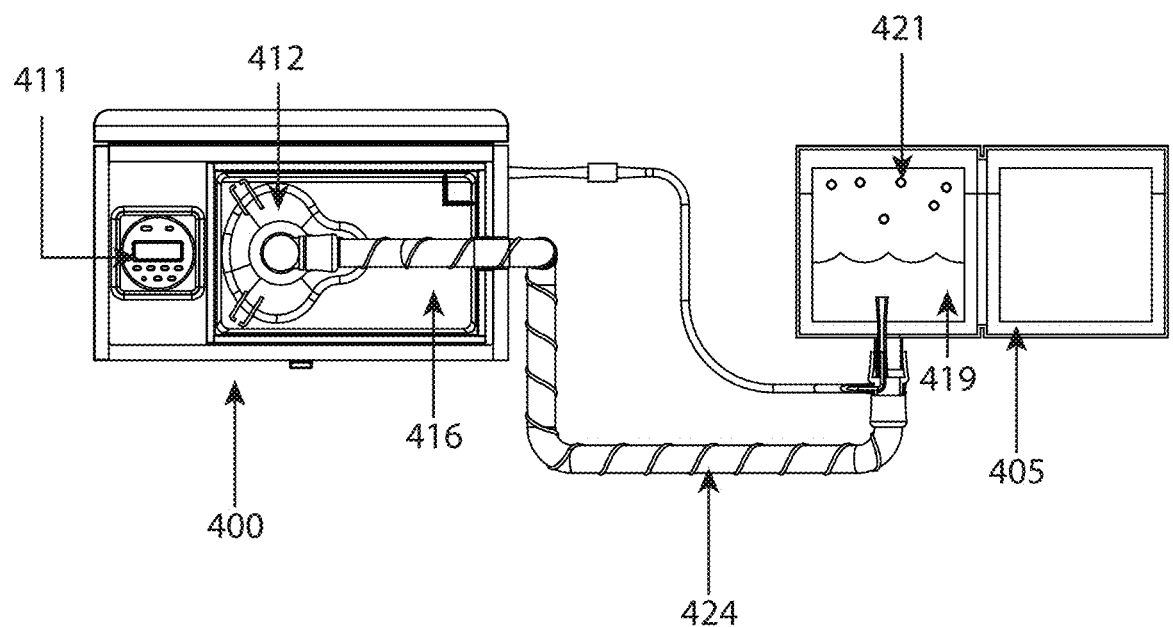
FIG. 4 is a top view of a water reservoir and hose with free ozone, in accordance with one embodiment of the present invention.

FIG. 4 shows a top view an ozone device 400 and a CPAP device 405 with the top covers removed for viewing the inner parts of the ozone device 400 and the CPAP device 405. In this embodiment, free ozone 421 is released from the water 419 and traverses into the hose 424. In accordance with the embodiment shown, the free ozone 421 will disinfect the water 419 and the hose 424. The free ozone 421 may continue to traverse from the hose 424 to the mask compartment 416 to further sanitize a mask 412, before exiting the ozone device 400 through an exhaust port. Further shown in this embodiment is a control panel 411 for a user to set ozone sanitizing schedules in accordance with a user's preferences.

Figure 5:
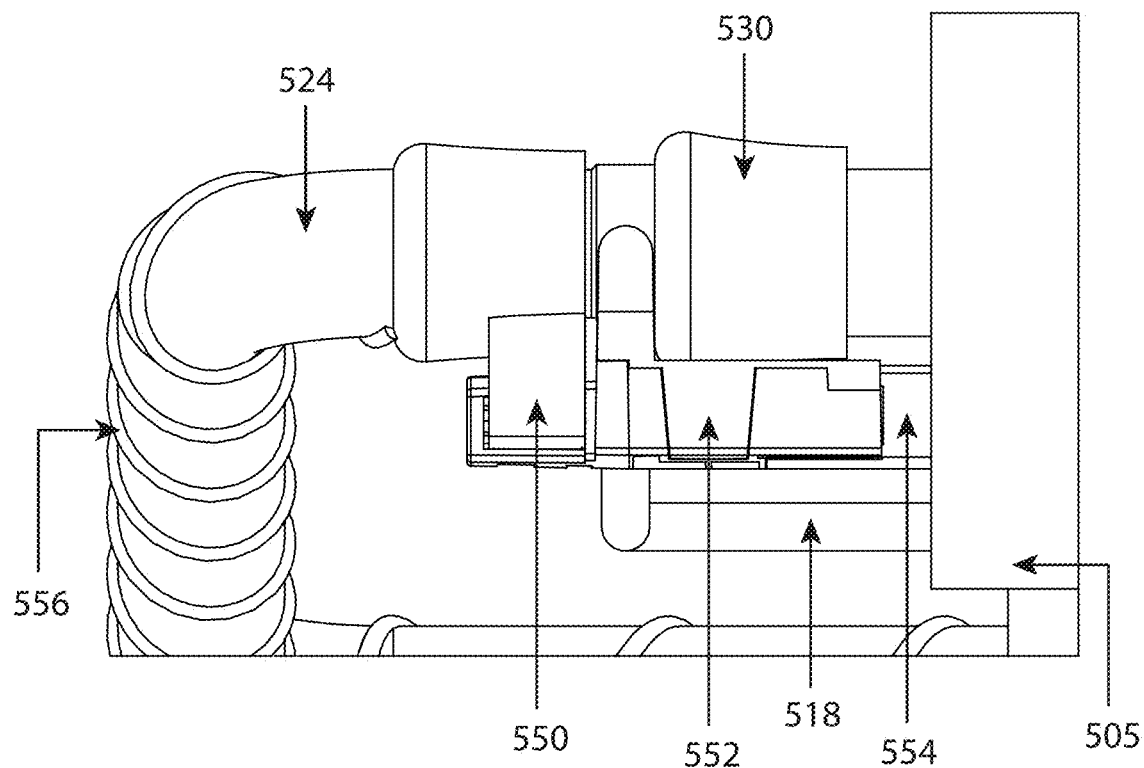
FIG. 5 is a side view of a CPAP connector unit and a heater adapter unit connecting a hose to a CPAP device in accordance with one embodiment of the present invention.

In another embodiment of the present invention, shown in FIG. 5, a heater adapter unit 552 is connected to a CPAP connector unit 530 to connect a heating element 550 on a hose 524 to a heating element receptors 554 on a CPAP device 505. The heating element 550 may be used to heat a hose 524, to prevent condensation of water vapor as it passes through the hose 524. While heating elements 550 are commonly used on CPAP devices 505, in order to practice the present invention of providing ozone to the CPAP device 505 through an ozone distribution line 518 for sanitizing a CPAP device 505, a heating adapter unit 552 may be required to attach the CPAP connector unit 530 to a CPAP device 505 with heating systems. One method of heating the hose 524 includes but is not limited to passing a low voltage electric current through a resistive conductor such as copper or aluminum conductor wires 556, which may be woven along the length of a hose 524 and effectively heat the hose 524, as shown in FIG. 5. Another method of heating the hose 524 may include using a hose sleeve of Neoprene or fleece to cover the exterior of the hose 524, which may insulate the hose from external cold air. FIG. 5 shows an embodiment with copper conductor wires 556 woven around the hose 524 for heating the hose 524. In this embodiment the heating element 550 contains copper conductor wires which connects to copper receptors in the heating element receptor 554, generating electric heat to copper conductor wires 556 when the CPAP device 505 is in an on position. In this embodiment a CPAP connector unit 530 is shown for connecting an ozone device in accordance with the present invention to a CPAP device 505 to disinfect the CPAP device between uses. The heater adapter unit 552 is connected to the CPAP connector unit 530 for attaching the heating element 550 to the heating element receptor 554, as shown. In accordance with this embodiment of the present invention, systems, methods and devices to provide ozone to sanitize a CPAP device 505, hose 524 and water reservoir may be used in conjunction with heating elements for heating the hose 524. In this embodiment, the CPAP connector unit 530 provides for the flow of ozone into an ozone distribution line 518 into a water reservoir, and then into the hose 524 from the water reservoir, while the heater adapter unit 552 connects the copper wires in the heating element 550 to the corresponding contacts in the heating element receptors 554 of the CPAP device 505.

Figure 5A:
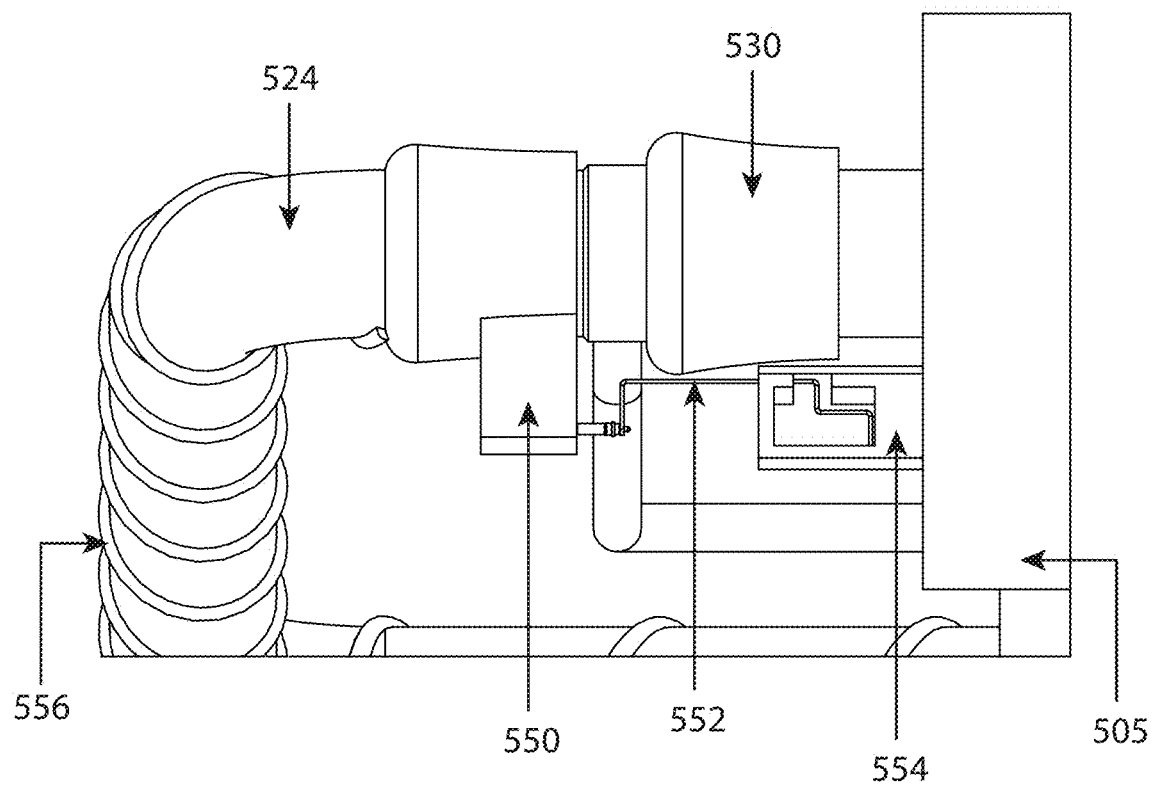
FIG. 5A is a side view of a CPAP connector unit and a heater adapter unit connecting a hose to a CPAP device in accordance with one embodiment of the present invention.

FIG. 5A shows in detail the connection of the copper wires in the heating elements 550 through the heating adapter unit 552 to the heater element receptors 554 on the CPAP device 505 in accordance with the embodiment described with reference to FIG. 5. In accordance with the embodiment shown, the heating adapter unit 552 is attached below the CPAP connector unit 530 and copper wires 556 are shown woven around the hose 524.

Figure 6:
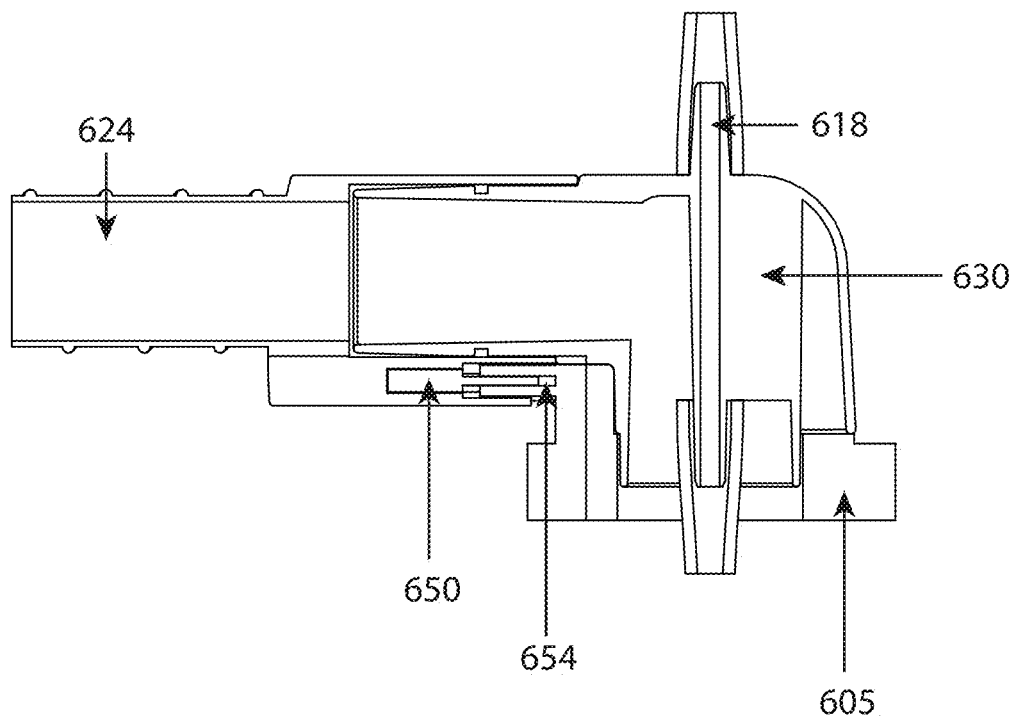
FIG. 6 is a side view of a CPAP device with a heating element, connected to the CPAP device with a continuous positive airway connector unit in accordance with one embodiment of the present invention.

FIG. 6 shows a side view of yet another embodiment of the present invention shown in FIG. 6 a CPAP connector unit 630 for connecting a heating element 650 heating system for heating a hose 624 of a CPAP device with a heating element 650 is shown. In this embodiment, cold air in a room may cause condensation of water vapor in the hose 624 of the CPAP device and results in bacterial growth in the hose and in a facial mask. Heating the hose 624 helps prevent condensation of water vapor in the hose 624. In accordance with this embodiment, a heating element 650 is formed at the end of the hose 624, where the hose 624 connects to a CPAP device. In this embodiment, a CPAP connector unit 630 is shown connecting the heating element 650 to the CPAP device 605 so that ozone may be further added to the CPAP device through the ozone distribution line in accordance with the present invention. In this embodiment the heating element 650 may work by passing a low voltage electric current through a resistive conductor which may be woven along the length of the hose effectively heating the hose.

Figure 7:
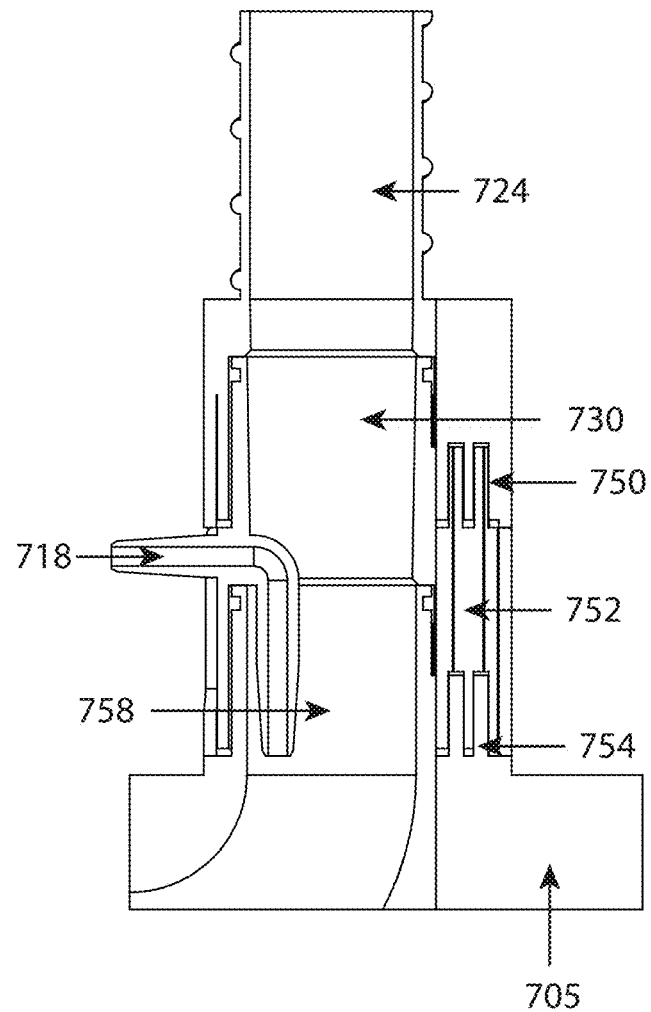
FIG. 7 is a side view of a CPAP device with a heating element, connected with a heater adapter unit in accordance with one embodiment of the present invention.

FIG. 7 shows a side view of yet another embodiment of the present invention shown in FIG. 7 a heating system for heating a hose 724 with a heating adapter unit 752 connected to a CPAP connector unit 730 to provide ozone to a CPAP device 705 with heating systems embedded therein is shown. In this embodiment, the heating receptors 754 are located adjacent to a hose on a CPAP device 705 and may contain copper wires to transfer electric power from the heating element 750, attached to the hose 724. In accordance with this embodiment, the heating adapter unit 752 fits over the CPAP hose entry 758 and the heating receptors 754 on the CPAP device 705 so that the ozone technology in accordance with the present invention may be connected through the ozone distribution line 718 to the CPAP device 705, while the heating elements 750 already in place on the CPAP device 705 may still be connected through the heating adapter unit 752 to heat the hose 724. In accordance with this embodiment, cold air in a room may cause condensation of water vapor in the hose 724 of the CPAP device and result in bacterial growth in the hose and a facial mask. Heating the hose 724 helps prevent condensation of water vapor in the hose 724, while administering ozone to the CPAP reservoir and hose in accordance with the present embodiment automatically disinfects the CPAP machine and prevents bacterial and mold build-up.

Figure 8:
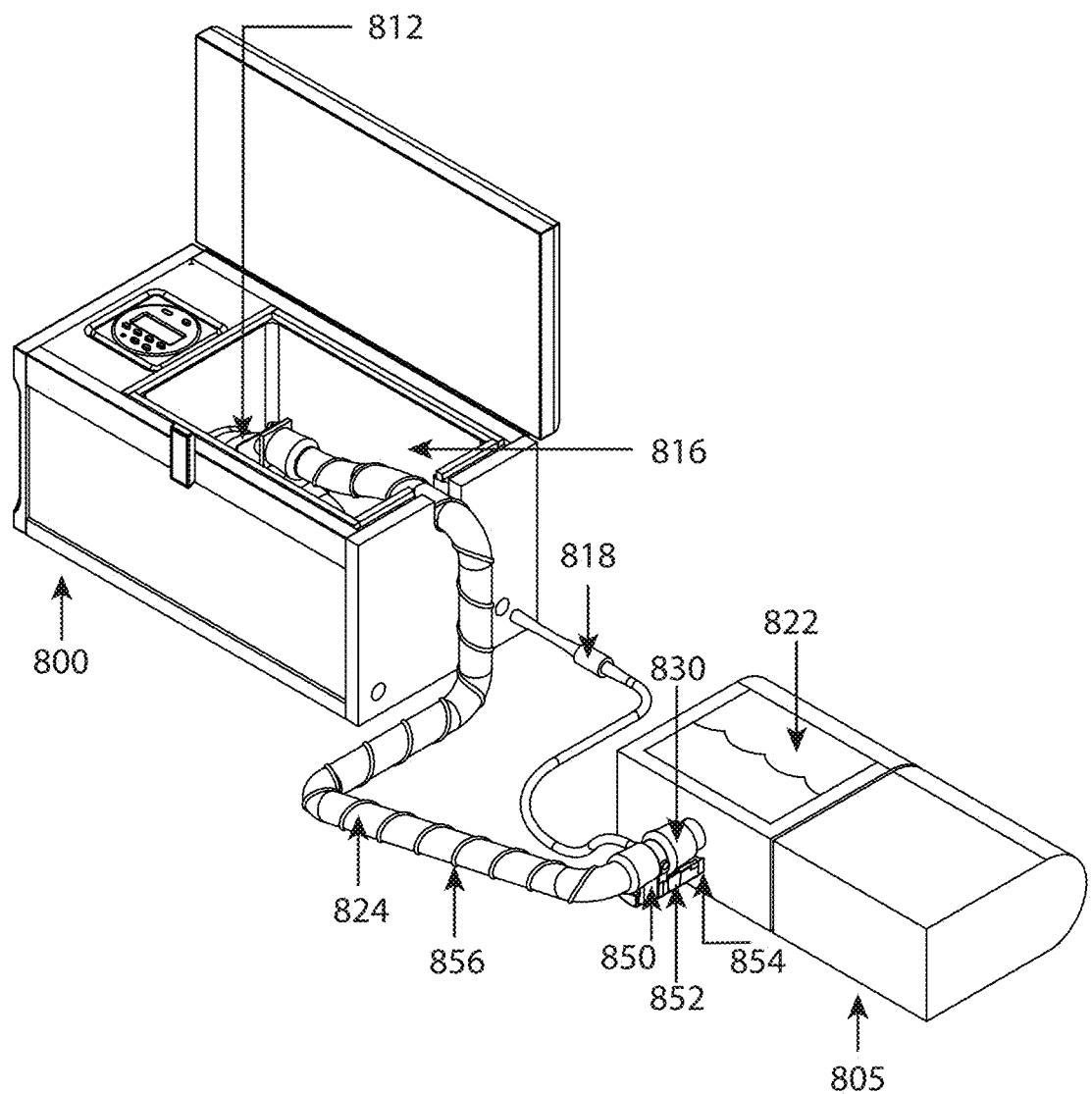
FIG. 8 is a perspective view of a CPAP device with a heating element connected to the CPAP device with a heater adapter unit.

FIG. 8 shows a perspective view of the present invention with the ozone device 800 connected to a CPAP device 805 with heating systems embedded in the CPAP device 805. In accordance with this embodiment, ozone is pumped from the ozone device 800 through an ozone distribution line 818 to the CPAP connector unit 830 to be released into the water reservoir 822. In this embodiment, a heating element 850 is provided on the hose 824 to connect to heating element receptors 854 on the CPAP device 805. In accordance with the embodiment shown, a heater adapter unit 852 is connected to the CPAP connector unit 830 to attach the heating element 850 to the heating element receptors 854. In accordance with this embodiment, the heating system may work to heat the hose 824 to prevent condensation of water during operation by heating copper wires 856 surrounding the hose. In addition, the ozone operating system in accordance with the present embodiment may sanitize the water reservoir 822, the hose 824, the mask 812 and the mask chamber 816 as shown.

In accordance with the embodiments shown, the ozone device will have a built-in timer so that a user can set the time to start the ozone disinfecting process at fixed time intervals. Typically, an ozone cycle is recommended at the end of each CPAP device use for best results for a consumer. The ozone device in accordance with one or more embodiments of the present invention will have a delayed start button, so that the CPAP device will not start until a fixed time has passed since the last ozone disinfecting process. In accordance with one or more embodiments, a one hour time period is implemented to prevent start of a CPAP device until one hour has passed from an ozone disinfecting process in accordance with one or more of the embodiments shown. In accordance with other embodiments a two-hour time period is implemented before the CPAP device can be used after an ozone disinfecting process in accordance with one or more embodiments of the present invention.

With reference to one or more embodiments shown, an ozone device is described including an ozone compartment, an ozone operating system, and one or more ozone distribution lines to distribute ozone through a CPAP device. A CPAP ozone air pump distributes ozone to the ozone distribution lines in one or more embodiments of the present invention. The ozone will migrate from the ozone distribution lines into the water reservoir of the CPAP device. The ozone will oxidize organic material in the water, thereby disinfecting water in the water reservoir. Remaining ozone will release as free ozone from the water reservoir and migrate as a gas into the attached hose, mask and mask compartment. An exhaust port in the mask compartment helps migrate free ozone into the hose, mask and mask compartment, and releases remaining ozone into the atmosphere as $O^2$ oxygen from the mask compartment. The ozone $O^3$ will disinfect the water reservoir, the hose, the mask and the mask compartment while the ozone migrates through the CPAP device in accordance with the embodiments of the present invention.

In addition to the device described and shown in the embodiments of the present invention, methods of disinfecting a CPAP device are further disclosed. In accordance with one embodiment, a method for disinfecting a continuous positive airway pressure may include the steps of producing ozone in an ozone device with an ozone operating system, releasing ozone into a continuous positive airway pressure device; and, migrating ozone through a continuous positive airway pressure device. In yet another embodiment, a method of disinfecting a CPAP device with an ozone device by releasing ozone into a CPAP connector unit, distributing ozone into a water reservoir, migrating free ozone from the water reservoir to a hose, migrating the free ozone into a mask in a mask compartment; and, removing the ozone from the CPAP device through an exhaust port, is described. The method disclosed further includes a step of delaying the start of a CPAP treatment for a fixed period of time from the last ozone disinfecting process for the safety of the consumers. The step of delaying the start time may range from about 30 minutes to 5 hours, depending on the embodiment implemented. In yet other embodiments the step of delaying the start time may range from about 5 hours to 10 hours. In addition the step of sensing remaining ozone in a CPAP device is an added step in one or more embodiments of the present invention for a consumer's safety prior to use. In addition, in one or more embodiments of the present invention, adding a safety switch in the mask compartment prevents starts of an ozone sanitizing process until the mask is returned by a user to the mask compartment. The safety switch is an additional precaution to prevent use of a CPAP device during an ozone disinfecting process.

Figure 9:
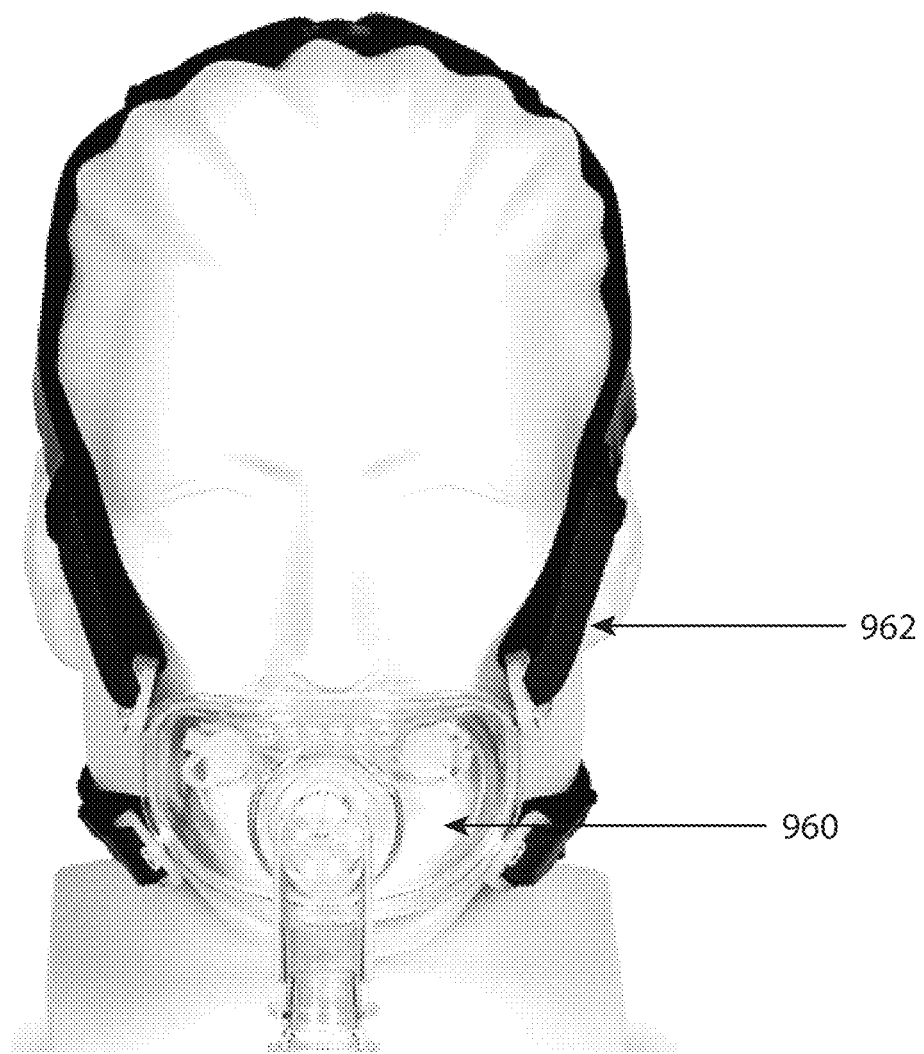
FIG. 9 is a front view of a CPAP mask, in accordance with a one embodiment of the present invention.

In yet another embodiment of the present invention, as shown in FIG. 9, an improved CPAP face mask 960 and straps 962 are provided to maximize comfort of a patient during a CPAP procedure. In accordance with the embodiment, the straps 962 are cut on a bias to maintain elasticity and fluidity of the straps 962 as the strap rests along a user's head and face during a CPAP procedure.

Figure 10:
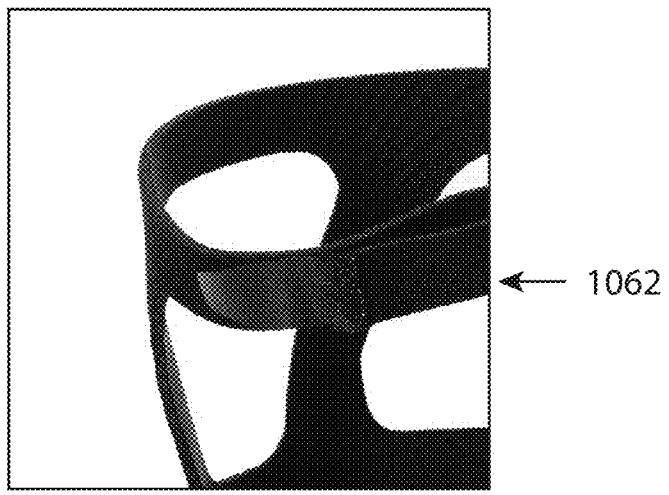
FIG. 10 is a side view of a CPAP mask and straps, in accordance with another embodiment of the present invention.

FIG. 10 shows another embodiment of the present invention, where a side view of a facemask straps 1062 are provided. In accordance with this embodiment, the straps 1062 are cut on a bias cut, to maximize the elastic comfort of the straps 1062 for a patient. In accordance with this embodiment, the straps 1062 is made of one or more material(s) that are lightweight, breathable, washable and disposable, for ease of use by a user.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

What is claimed is:

1. A system comprising:
   a housing
   an ozone device disposed within the housing and configured to generate ozone gas;
   an ozone distribution line located external to the housing;
   a connector unit comprising a first end, a second end, and a port; and
   a chamber disposed within the housing;
   wherein:
   the distribution line is configured to fluidly couple to the ozone device, and to fluidly couple to the connector unit via the port;
   the first end of the connector unit is configured to couple to a continuous positive airway pressure (CPAP) device;
   the second end of the connector unit is configured to couple to a first end of a CPAP hose;
   the chamber is configured to receive at least a CPAP mask and to fluidly couple to a second end of the CPAP hose; and
   the connector unit is configured to receive a flow of ozone gas from the ozone distribution line and to convey ozone gas to the CPAP hose.

2. The system of claim 1, further comprising said CPAP device and said CPAP hose, wherein:
   the first end of the connector unit is coupled directly to the CPAP device;
   the second send of the connector unit is coupled directly to the first end of the CPAP hose;
   the port is fluidly coupled to the ozone distribution line; and
   the second end of the CPAP hose is fluidly coupled to the chamber.

3. The system of claim 2, wherein said CPAP device comprises a water reservoir and said connector unit is in fluid communication with said water reservoir.

4. The system of claim 3, wherein said chamber comprises a lid and at least one wall, wherein the lid is movable between an open position and a closed position.

5. The system of claim 3, further comprising:
an exhaust port fluidly coupled to said chamber, wherein the exhaust port is to exhaust ozone gas from said chamber; and
a filter for converting ozone to oxygen fluidly coupled to the exhaust port.

6. The system of claim 2, wherein the port is coupled directly to the distribution line.

7. The system of claim 1, wherein the chamber comprises an exhaust port.

8. The system of claim 7, further comprising a filter for converting ozone gas to oxygen in the exhaust port.

9. A system comprising:
a continuous positive airway pressure (CPAP) device;
a CPAP hose;
an ozone device configured to generate ozone gas;
an ozone distribution line;
a connector unit comprising a first end, a second end, and a port;
a chamber;
wherein:
the distribution line is configured to fluidly couple to the ozone device;
the first end of the connector unit is coupled directly to the CPAP device;
the second end of the connector unit is coupled to a first end of the CPAP hose;
the port is fluidly coupled to the ozone distribution line;
the chamber is configured to receive at least a CPAP mask and is fluidly coupled to a second end of the CPAP hose; and
the connector unit is configured to receive a flow of ozone gas from the ozone distribution line and to convey ozone gas to the CPAP hose.

10. A method of sanitizing a device with a water reservoir, the method comprising:
connecting a proximal end of a distribution line to an ozone device within a housing, the distribution line being external to the housing;
fluidly coupling a distal end of the distribution line to a port of a connector unit, the connector unit further comprising a first end coupled to a continuous positive airway pressure (CPAP) device and a second end coupled to a first end of a CPAP hose, wherein a second end of the CPAP hose is fluidly coupled to a chamber that is within the housing and is configured to receive at least a CPAP mask;
generating ozone gas with said ozone device;
flowing said ozone gas from said ozone operating system, outside said housing to said distribution line, through said distribution line, and through said port; and
flowing ozone gas from said water reservoir, into said hose, and into said chamber.

11. The method of claim 10, further comprising flowing ozone gas through an exhaust port in said chamber and converting ozone gas to oxygen with a filter.

12. The method of claim 10, wherein:
said first end of said connector unit is coupled directly to said CPAP device: and
said second end of said connector unit is coupled directly to said first end of said CPAP hose.

13. The method of claim 12, wherein the port is coupled directly to the distribution line.

14. The system of claim 10, wherein said chamber comprises a lid and at least one wall, wherein the lid is movable between an open and a closed position.

15. The system of claim 10, wherein the port is coupled directly to the distribution line.

16. The method of claim 10, wherein:
said first end of said connector unit is coupled directly to said CPAP device;
said second end of said connector unit is coupled directly to said first end of said CPAP hose; and
the port is coupled directly to the distribution line.

* * * * *